United States Patent [19]

Chucholowski et al.

[11] Patent Number: 4,868,185

[45] Date of Patent: Sep. 19, 1989

[54] 6-[[(SUBSTITUTED)PYRIMIDINYL)ETHYL]- AND ETHENYL]TETRAHYDRO-4-HYDROXYPYRAN-2-ONE INHIBITORS OF CHOLESTEROL BIOSYNTHESIS

[75] Inventors: Alexander W. Chucholowski, Ypsilanti; Bruce D. Roth, Ann Arbor; Drago R. Sliskovic, Ypsilanti, all of Mich.

[73] Assignee: Warner-Lambert Company, Morris Plains, N.J.

[21] Appl. No.: 130,870

[22] Filed: Dec. 10, 1987

[51] Int. Cl.$^4$ .......................................... A61K 31/505
[52] U.S. Cl. ................................... 514/256; 544/296; 544/333
[58] Field of Search ................. 544/333, 296; 514/256

[56] References Cited

U.S. PATENT DOCUMENTS

| | | | |
|---|---|---|---|
| 4,613,610 | 9/1986 | Wareing | 514/406 |
| 4,647,576 | 3/1987 | Hoefle et al. | 514/422 |
| 4,668,794 | 5/1987 | Wareing | 548/342 |
| 4,681,893 | 7/1987 | Roth | 514/422 |

FOREIGN PATENT DOCUMENTS

WO84/02131  6/1984  PCT Int'l Appl. ................ 514/367

*Primary Examiner*—Mary C. Lee
*Assistant Examiner*—Zinna Northington
*Attorney, Agent, or Firm*—Ronald A. Daignault

[57] ABSTRACT

Certain trans-6-[[(substituted)pyrimidin-5-yl]ethyl]- and ethenyl]tetrahydro-4-hydroxypyran-2-ones and the corresponding dihydroxy ring-opened acids derived therefrom are potent inhibitors of the enzyme 3-hydroxy-3-methylglutaryl-coenzyme A reductase (HMG-CoA reductase) and are useful as hypocholesterolemic and hypolipidemic agents.

8 Claims, No Drawings

6-[[SUBSTITUTED)PYRIMIDINYL)ETHYL]- AND ETHENYL]TETRAHYDRO-4-HYDROXYPYRAN-2-ONE INHIBITORS OF CHOLESTEROL BIOSYNTHESIS

BACKGROUND OF THE INVENTION

The present invention is related to compounds and pharmaceutical compositions useful as hypocholesterolemic and hypolipidemic agents. More particularly, this invention concerns certain trans-6-[[(substituted)-pyrimidin-5-yl]ethyl]- and ethenyl]tetrahydro-4-hydroxypyran-2-ones and the corresponding dihydroxy ring-opened acids which are potent inhibitors of the enzyme 3-hydroxy-3-methylglutaryl-coenzyme A reductase (HMG-CoA reductase), pharmaceutical composition containing such compounds, and a method of lowering blood serum cholesterol levels employing such pharmaceutical compositions.

High levels of blood cholesterol and blood lipids are conditions which are involved in the onset of arteriosclerosis. It is well known that inhibitors of HMG-CoA reductase are effective in lowering the level of blood plasma cholesterol, especially low density lipoprotein cholesterol (LDL-C), in man (cf. M. S. Brown and J. L. Goldstein, *New England Journal of Medicine* (1981), 305, No. 9, 515–517). It has now been established that lowering LDL-C levels affords protection from coronary heart disease (cf. *Journal of the American Medical Association* (1984) 251, No. 3, 351–374).

Moreover, it is known that certain derivatives of mevalonic acid (3,5-dihydroxy-3-methylpentanoic acid) and the corresponding ring-closed lactone form, mevalonolactone, inhibit the biosynthesis of cholesterol (cf. F. M. Singer et al, *Proc. Soc. Exper. Biol. Med.* (1959), 102, 270) and F. H. Hulcher, *Arch. Biochem. Biophys.* 30 (1971), 146, 422.

U.S. Pat. Nos. 3,983,140; 4,049,495 and 4,137,322 disclose the fermentative production of a natural product, now called compactin, having an inhibitory effect on cholesterol biosynthesis. Compactin has been shown to have a complex structure which includes a mevalonolactone moiety (Brown et al, *J. Chem. Soc. Perkin I*, (1976), 1165.

U.S. Pat. No. 4,255,444 to Oka et al discloses several synthetic derivatives of mevalonolactone having antilipidemic activity.

U.S. Pat. Nos. 4,198,425 and 4,262,013 to Mitsue et al disclose aralkyl derivatives of mevalonolactone which are useful in the treatment of hyperlipidemia.

U.S. Pat. No. 4,375,475 to Willard et al discloses certain substituted 4-hydroxytetrahydropyran-2-ones which, in the 4(R)-trans-stereoisomeric form, are inhibitors of cholesterol biosynthesis.

U.S. Pat. No. 4,647,576 to Hoefle, et al discloses certain trans-6-[2-[(substituted)-pyrrol-1-yl]alkyl]tetrahydro-4-hydrolpyran-2-ones and the corresponding lactone ring-opened acids as inhibitors of cholesterol biosynthesis.

U.S. Pat. No. 4,681,893 to Roth discloses certain trans-6-[[(2-, (3-, or (4-carboxamido-substituted)pyrrol-1-yl]alkyl- or alkenyl]-tetrahydro-4-hydroxypyran-2-one inhibitors of cholesterol biosynthesis.

SUMMARY OF THE INVENTION

In accordance with the present invention, there are provided certain trans-6-[[2-(substituted)pyrimidinyl]ethyl- or ethenyl]tetrahydro-4-hydroxypyran-2-ones and the corresponding ring-opened hydroxy-acids which are potent inhibitors of cholesterol biosynthesis by virtue of their ability to inhibit the enzyme 3-hydroxy-3-methylglutaryl coenzyme A reductase (HMG-CoA reductase).

In particular, in its broadest chemical compound aspect, the present invention provides compounds of structural Formula I

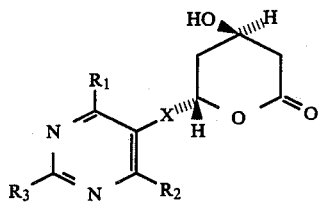

wherein X is —CH2CH2—or —CH=CH—(preferably in the trans configuration).

R1 and R2 are independently selected from hydrogen; alkyl of from one to six carbons; alkoxy of from one to four carbon atoms; trifluoromethyl; cyclopropyl; cyclohexyl; cyclohexylmethyl; phenyl; phenyl substituted with fluorine, chorine, bromine, hydroxy, trifluoromethyl, alkyl of from one to four carbon atoms, or alkoxy of from one to four carbon atoms; phenylmethyl; or phenylmethyl substituted with fluorine, chlorine, bromine, hydroxy, trifluoromethyl, alkyl of from one to four carbon atoms, or alkoxy of from one to four carbon atoms.

R3 is hydrogen; alkyl of from one to six carbon atoms; trifluoromethyl; cyclopropyl; phenyl; or phenyl substituted with fluorine, chlorine, bromine, hydroxy, trifluoromethyl, alkyl of from one to four carbon atoms, or alkoxy of from one to four carbon atoms.

Also contemplated as falling within this aspect of the invention are the corresponding dihydroxy-acid compounds of Formula II corresponding to the opened form of the lactone ring of compounds of Formula I

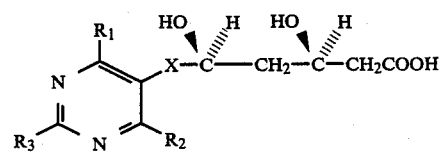

where X, R1, R2, and R3 are as defined above, and the pharmaceutically acceptable salts thereof, all of the compounds being in the trans racemate of the tetrahydropyran moiety.

In another aspect of the present invention, there is provided a method of preparing compounds of Formula I above by (a) first reacting a substituted [(pyrimidin-5-yl)ethyl- or ethenyl]aldehyde compound of Formula III

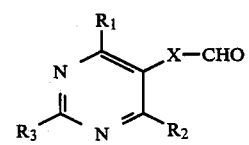

where X, R1, R2, and R3, are as defined above, with the alkali metal salt of the dianon of ethyl acetoacetate to form a compound of structural Formula IV

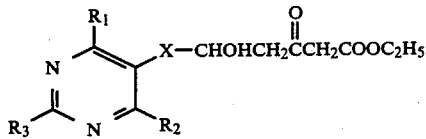

where X, $R_1$, $R_2$, and $R_3$, are as defined above, then successively (b) reducing Compound IV with a trialkylborane and sodium borohydride and (c) oxidizing with alkaline hydrogen peroxide to produce an ester compound of Formula V

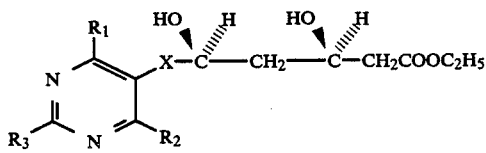

and finally (d) hydrolyzing and cyclizing, if desired, the ester compound of Formula V to a lactone compound of Formula I by heating in an inert solvent or, alternatively converting, if desired, the intermediate dihydroxy acid thus formed to a pharmaceutically acceptable salt.

In another aspect, the present invention provides pharmaceutical compositions, useful as hypolipidemic or hypocholesterolemic agents, comprising a hypolipidemic or hypocholesterolemic affective amount of a compound in accordance with this invention as set forth above, in combination with a pharmaceutically acceptable carrier.

In another aspect, the present invention provides a method of inhibiting cholesterol biosynthesis in a patient in need of such treatment by administering a pharmaceutical composition in accordance with the present invention as defined above.

DETAILED DESCRIPTION

Preferred compounds of the invention are those in which X is —CH=CH—. Preferred substituent groups for $R_1$ are phenyl and substituted phenyl, while preferred groups for $R_2$ are alkyl or cycloalkyl. Phenyl and substituted phenyl groups are preferred for $R_3$.

As used throughout this specification and the appended claims, the term "alkyl" denotes a branched or unbranched substituted hydrocarbon group derived by the removal of one hydrogen atom from an alkane. The term "lower alkyl" denotes alkyl of from one to four carbon atoms.

The term "alkoxy" denotes an alkyl group, as just defined, attached to the parent molecular residue through an oxygen atom.

Particularly preferred compounds of the present invention include the following:

[4α,6β(E)]-6-[2-[4-(4-Fluorophenyl)-2,6-dimethyl-5-pyrimidinyl]ethenyl]tetrahydro-4-hydroxy-2H-pyran-2-one.

[4α,6β(E)]-6-[2-[4-(4-Fluorophenyl)-6-methyl-2-phenyl-5-pyrimidinyl]ethenyl]tetrahydro-4-hydroxy-2H-pyran-2-one.

[4α,6β(E)]-6-[2-[4-(3,5-Dimethylphenyl)-6-methyl-2-phenyl-5-pyrimidinyl]ethenyl]tetrahydro-4-hydroxy-2H-pyran-2-one.

[R*,S*-(E)]-7-[4-(4-Fluorophenyl)-2,6-dimethyl-5-pyrimidinyl]-3,5-dihydroxy-6-heptenoic acid.

[R*,S*-(E)]-7-[4-(4-Fluorophenyl)-6-methyl-2-phenyl-5-pyrimidinyl]-3,5-dihydroxy-6-heptenoic acid.

[R*,S*-(E)]-7-[4-(3,5-Dimethylphenyl)-6-methyl-2-phenyl-5-pyrimidinyl]-3,5-dihydroxy-6-heptenoic acid.

Compounds of the present invention are prepared by the general synthetic methods outlined in the following Reaction Scheme. Referring to the Reaction Scheme, the β-ketoester, represented by ethyl acetoacetate, is condensed with the desired carboxaldehyde, represented by Reaction Sequence

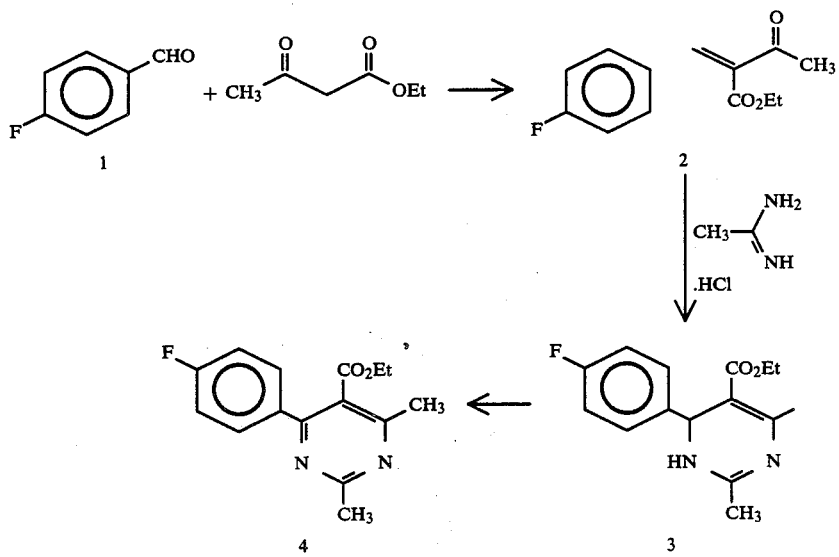

-continued
Reaction Sequence
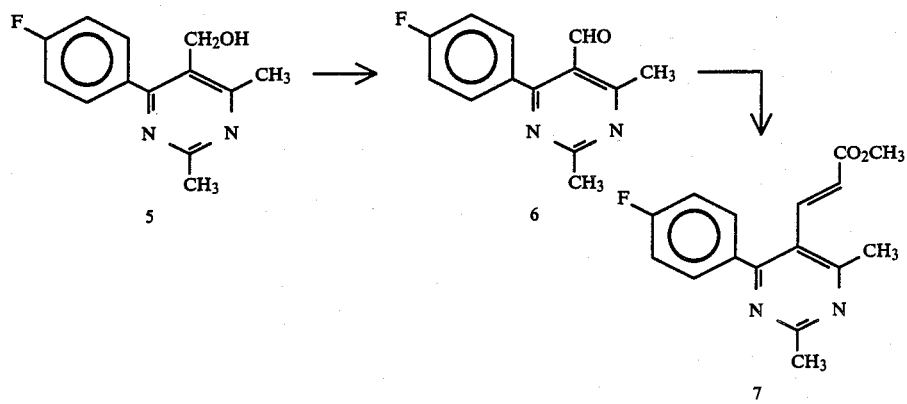
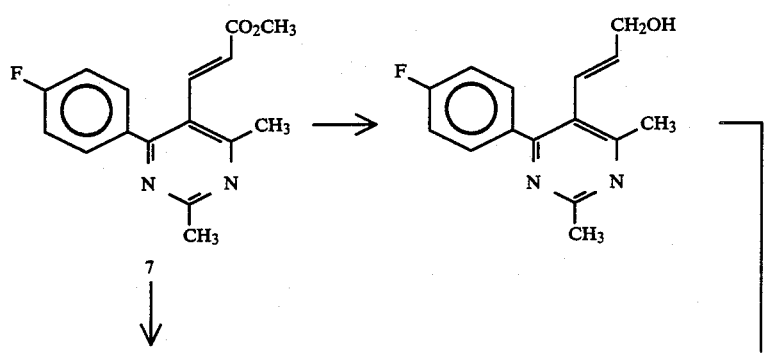
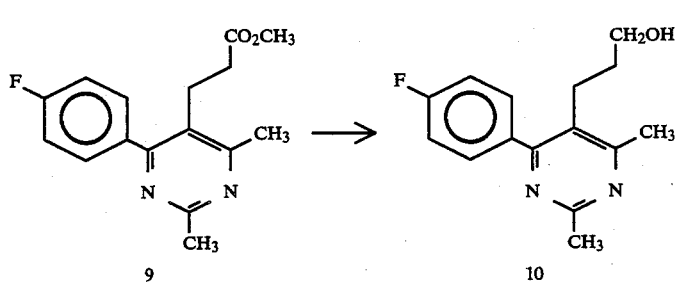
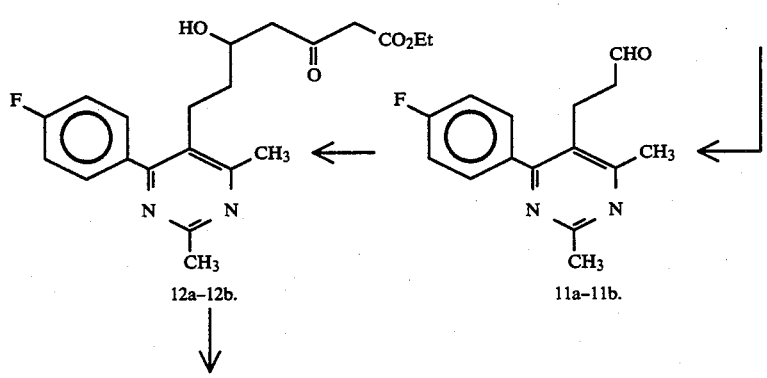

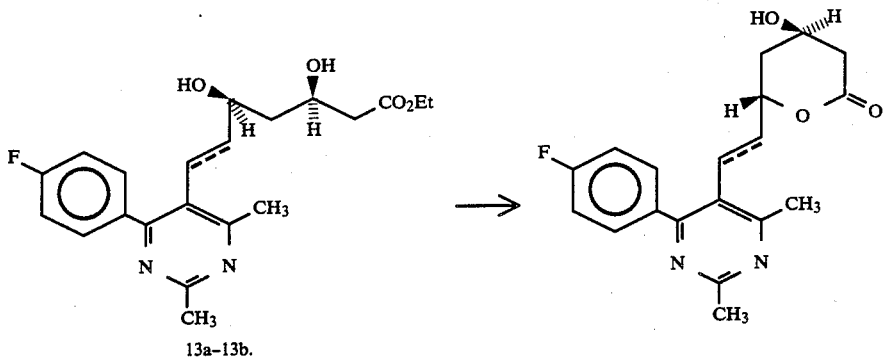

13a–13b.

4-fluorobenzaldehyde, 1, to produce the condensation product 2. This reaction is generally carried out in toluene under reflux with azeotropic removal of water, and in the presence of a base such as piperidine acetate (formed in situ from piperidine and glacial acetic acid).

The condensation product, 2, is further condensed with the desired amidine, represented in the reaction scheme by acetamidine hydrochloride. Ureas, thioureas, and guanidines may also be employed in this reaction. The reaction is generally carried out in a high-boiling alcoholic solvent such as n-butanol under reflux in the presence of a base such as triethylamine.

The resulting dihydropyrimidine, 3, is next aromatized to the pyrimidine, 4, by heating with powdered sulfur for a period of 1–3 hours in the absence of a solvent, generally at a temperature of about 130°–150° C.

Compound 4 is then reduced by the action of diisobutyl aluminum hydride (DIBAL) in dichloromethane at −78° C. to produce the alcohol, 5. The alcohol, 5 is then oxidized to the corresponding aldehyde, 6, by the method of Swern (Swern, et al, *J. Org. Chem.*, 43:2480 (1978)). This reaction is generally carried out in dichloromethane at −78° C.

Wittig reaction of the aldehyde, 6, with an ylide such as methyl(triphenylphosphoranylidene) acetate in methylene chloride at room temperature produces the trans-ester, 7, in high yield. The ester, 7, is reduced to the corresponding alcohol, 8, using two equivalents of diisobutyl aluminum hydride at −78° C.

Alternatively, the unsaturated ester, 7, is reduced over Pd/C by the action of hydrogen to produce the saturated ester, 9, which is then reduced by the action of DIBAL to produce the corresponding alcohol which is then carried forward in the sequence of steps to produce the product having the saturated ethyl bridge (X=ethylene in generic Formula I).

The alcohols, 8 or 10, are oxidized to the corresponding aldehydes, 11a or 11b, by Swern oxidation, followed by an aldol condensation with the sodium lithium dianion of ethyl acetoacetate at −78° C. in tetrahydrofuran (See Kraus, et al, *J. Org. Chem.*, 48: 2111 (1983) to form the 5-hydroxy-3-oxo-6-heptenoic acid esters, 12a, and 12b.

The product of this condensation is then reduced in a sequence of steps in which it is first dissolved in a polar solvent such as tetrahydrofuran under a dry atmosphere. A small excess of triethylborane and catalytic amounts of 2,2-dimethylpropanoic acid are next added. The mixture is stirred at room temperature for a short period, after which it is cooled to a temperature preferably between about −60° C. and −80° C. Dry methanol is added, followed by sodium borohydride. The mixture is kept at low temperature for 4–8 hours before treating it with hydrogen peroxide and ice water. The substituted 3,5-dihydroxy-6-heptenoic acid ethyl esters, 13a and 13b, are isolated having the preferred R*, S* and R*, R* configurations, respectively.

The esters, 13a and 13b, may be utilized as such in the pharmaceutical method of this invention, or may be converted, if desired, the the corresponding acid salt forms, such as the sodium salt, employing basic hydrolysis by generally well-known methods. The free acids, produced by neutralization of the sodium salts, can be dehydrated to the lactone, I by heating the acids in an inert solvent such as toluene with concomitant azeotropic removal of water.

In the ring-opened dihydroxy acid form, compounds of the present invention react to form salts with pharmaceutically acceptable metal and amine cations formed from organic and inorganic bases.

The term "pharmaceutically acceptable metal cation" contemplates positively charge metal ions derived from sodium, potassium, calcium, magnesium, aluminum, iron, zinc and the like.

The term "pharmaceutically acceptable amine cation" contemplates the positively charged ions derived from ammonia and organic nitrogenous bases strong enough to form such cations. Bases useful for the formation of pharmaceutically acceptable nontoxic base addition salts of compounds of the present invention form a class whose limits are readily understood by those skilled in the art. (See, for example, Berge, et al, "Pharmaceutical Salts," *J. Pharm. Sci.*, 66:1–19 (1977)).

The free acid form of the compound may be regenerated from the salt, if desired, by contacting the salt with a dilute aqueous solution of an acid such as hydrochloric acid.

The base addition salts may differ from the free acid form of compounds of this invention in such physical characteristics as melting point and solubility in polar solvents, but are considered equivalent to the free acid forms for purposes of this invention.

The compounds of this invention can exist in unsolvated as well as solvated forms. In general, the solvated forms, with pharmaceutically acceptable solvents such as water, ethanol, and the like, are equivalent to the unsolvated forms for purposes of this invention.

The compounds of this invention are useful as hypocholesterolemic or hypolipidemic agents by virtue of their ability to inhibit the biosynthesis of cholesterol through inhibition of the enzyme 3-hydroxy-3-methylglutaryl-coenzyme A reductase (HMG-CoA reductase).

The ability of compounds of the present invention to inhibit the biosynthesis of cholesterol was measured by a method (designated CSI screen) which utilizes the procedure described by R. E. Dugan et al, *Archiv. Biochem. Biophys.*, (1972), 152, 21–27. In this method, the level of HMG-CoA enzyme activity in standard laboratory rats is increased by feeding the rats a chow diet containing 5% cholestyramine for four days, after which the rats are sacrificed.

The rat livers are homogenized, and the incorporation of 14C-acetate into nonsaponifiable lipid by the rat liver homogenate is measured. The micromolar concentration of compound required for 50% inhibition of sterol synthesis over a one-hour period is measured, and expressed as an IC50 value.

The activities of several representative examples of compounds in accordance with the present invention appear in Table 1.

For preparing pharmaceutical compositions from the compounds described by this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with finely divided active compound. In tablets, the active compound is mixed with the carrier having the necessary binding properties in suitable proportions and

TABLE 1

| X | $R_1$ | $R_2$ | $R_3$ | CSI IC$_{50}$ μMole/Liter |
|---|---|---|---|---|
| —CH═CH— | 4-Fluorophenyl | CH$_3$ | Phenyl | 0.15 |
| —CH═CH— | 3,5-Dimethylphenyl | CH$_3$ | Phenyl | 0.22 |
| —CH═CH— | 4-Fluorophenyl | CH$_3$ | CH$_3$ | 0.13 | compacted in the shape and size desired.

For preparing suppository preparations, a low-melting wax such as a mixture of fatty-acid glycerides and cocoa butter is first melted, and the active ingredient is dispersed homogeneously therein, as by stirring. The molten homogeneous mixture is then poured into convenient sized molds and allowed to cool and solidify.

The powders and tablets preferably contain 5 to about 70% of the active ingredient. Suitable solid carriers are magnesium carbonate, magnesium stearate, talc, sugar, lactose, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as carrier providing a capsule in which the active component (with or without other carriers) is surrounded by a carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions for oral use can be prepared by dissolving the active component in water and adding suitable colorants, flavoring agents, stabilizers, and thickening agents as desired. Aqeous suspensions for oral use can be made by dispersing the finely divided active component in water with viscous material, i.e., natural or synthetic gums, resins, methyl, cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or table itself or it can be the appropriate number of any of these packaged forms.

In therapeutic use as hypolipidemic or hypocholesterolemic agents, the compounds utilized in the pharmaceutical method of this invention are administered to the patient at dosage levels of from 40 mg to 600 mg per day. For a normal human adult of approximately 70 kg or body weight, this translates to a dosage of from about 0.5 mg/kg to about 8.0 mg/kg of body weight per day.

The dosages, however, may be varied depending upon the requirements of the patient, the severity of the condition being treated, and the compound being employed. Determination of optimum dosages for a particular situation is within the skill of the art.

The following examples illustrate particular methods for preparing compounds in accordance with this invention. These examples are illustrative and are not to be read as limiting the scope of the invention as it is defined by the appended claims.

EXAMPLE 1

Preparation of [R*, S*(E)]-7-[4-(4-Fluorophenyl)-2,6-dimethyl-5-pyrimidinyl]-3,5-dihydroxy-6-heptenoic acid and [4α,6β(E)]-6-[2-[4-(4-Fluorophenyl)-2,6-dimethyl-5-pyrimidinyl]ethenyl]tetrahydro-4-hydroxy-2H-pyran-2-one Step 1 - Preparation of ethyl 2-[(4-fluorophenyl)methylene]-3-oxobutanoate Piperidine (4.0 mL) and glacial acetic acid (12 mL) were added to a stirred solution of ethyl acetoacetate (127.5 mL, 1.0 mol) and 4-fluorobenzaldehyde (136.52 g, 1.1 mol) in 200 mL of toluene. This mixture was heated under reflux for four hours with azeotropic removal of water. The reaction mixture was cooled to room temperature and concentrated. The residue was flash chromatographed on silica gel, eluting with toluene, to produce 226.0 g of crude product which was then distilled to yield 186.2 g of a mixture of cis- and trans-ethyl 2-[(4-fluorophenyl)methylene]-3-oxobutanoate, bp 160°–170° C. at 5 mm Hg.

Proton NMR spectrum (CDCl₃): δ1.0–1.3 (triplet, 3 protons), δ2.2 (singlet, 3 protons), δ4.0–4.3 (quartet, 2 protons), and δ6.7–7.0 (multiplet, 3 protons).

Step 2 - Preparation of ethyl 6-(4-fluorophenyl)-1,6-dihydro-2,4-dimethyl-5-pyrimidinecarboxylate To a solution of 100 g (0.42 mol) of cis- and trans-ethyl 2-[(4-fluorophenyl)methylene]-3-oxo-butanoate in 700 mL of n-butanol was added, with stirring, 48.0 g (0.502 mol) of acetamidine hydrochloride and 58.3 g (0.576 mol) of triethylamine. The resulting mixture was heated under reflux for two hours and then cooled to room temperature and concentrated under vacuum.

The residue was partitioned between ethyl acetate and 1M hydrochloric acid solution. The organic layer was extracted with 1M hydrochloric acid solution and the combined acid solutions were washed with diethyl ether and then made basic with saturated potassium carbonate solution. The basic solution was extracted with ethyl acetate, the organic layer filtered and concentrated to yield 75.7 g of ethyl 6-(4-fluorophenyl)-1,6-dihydro-2,4-dimethyl-5-pyrimidinecarboxylate.

Proton NMR spectrum (CDCl₃): δ1.0–1.3 (triplet, 3 protons), δ1.8 (singlet, 3 protons), δ2.2 (triplet, 3 protons), δ3.9–4.1 (quartet, 2 protons), δ5.4 (singlet, 1 proton), 6.8–7.4 (multiplet, 4 protons), and 8.1–8.4 (broad singlet, 1 proton).

Step 3 - Preparation of ethyl 4-(4-fluorophenyl)-2,6-dimethyl-5-pyrimidinecarboxylate Ethyl 6-(4-fluorophenyl)-1,6-dihydro-2,4-dimethyl-5-pyrimidinecarboxylate (75.7 g, 0.274 mol) and 9.67 g (0.3 mol) of powdered sulfur were heated together at 130°–150° C. for three and one-half hours. After hydrogen sulfide evolution had ceased, the melt was cooled to room temperature and flash chromatographed on silica gel, eluting with 10% ethyl acetate/hexane, to yield 48.7 g of ethyl 4-(4-fluorophenyl)-2,6-dimethyl-5-pyrimidinecarboxylate.

Proton NMR spectrum (CDCl₃): δ1.0 (triplet, 3 protons), δ2.5 (singlet, 3 protons), δ2.6 (singlet, 3 protons), δ4.1 (quartet, 2 protons), and δ7.5–7.7 (multiplet, 2 protons).

Step 4 - Preparation of 4-(4-fluorophenyl)-2,6-dimethyl-5-pyrimidinemethanol To a solution of 46.5 g (0.169 mol) of ethyl 4-(4-fluorophenyl)-2,6-dimethyl-5-pyrimidinecarboxylate in 500 mL of dichloromethane at −78° C. under nitrogen was added 340 mL of a 1M solution of diisobutylaluminum hydride (0.339 mol) in dichloromethane. The resulting mixture was stirred at -78° C. for one-half hour and then the reaction was quenched by the addition of a saturated aqueous solution of sodium sulfate (48.15 g, 0.34 mol). The cooling bath was removed and the mixture was vigorously stirred for twenty minutes and then filtered through Celite®. The filter cake was thoroughly washed with chloroform and the combined filtrate and washings were dried over anhydrous magnesium sulfate and evaporated to yield 31.14 g of 4-(4-fluorophenyl)-2,6-dimethyl-5-pyrimidinemethanol, mp 174°–176° C.

Proton NMR spectrum (CDCl₃): δ2.2 (triplet, 1 proton), δ2.6 (singlet, 3 protons), δ2.65 (singlet, 3 protons), δ4.55 (doublet, 2 protons), δ7.0–7.2 (multiplet, 2 protons), and δ7.5–7.7 (multiplet, 2 protons).

Step 5 - Preparation of 4-(4-fluorophenyl)-2,6-dimethyl-5-pyrimidinecarboxaldehyde To a solution of 12.9 mL (0.147 mol) of oxalyl chloride in 250 mL of dichloromethane at −78° C. under nitrogen was added dropwise, over a period of two minutes, a solution of 21 mL (0.295 mol) of dimethylsulfoxide in 20 mL of dichloromethane. 4-(4-Fluorophenyl)-2,6-dimethyl-5-pyrimidinemethanol (31.14 g, 0.134 mol) in 150 mL of dichloromethane and 50 mL of dimethylsulfoxide was added dropwise over a period of twenty-five minutes.

The resulting mixture was stirred for an additional twenty minutes at −78° C. and then 93.2 mL (0.67 mol) of triethylamine was added and the cooling bath was removed. The solution was then allowed to warm to room temperature and 200 mL of a saturated aqueous solution of ammonium chloride was added. The mixture was stirred vigorously, chloroform was added, and the phases separated. The organic layer was washed successively with water and brine solution, dried over anhydrous magnesium sulfate, filtered, and evaporated to yield 31.0 g of 4-(4-fluorophenyl)-2,6-dimethyl-5-pyrimidinecarboxaldehyde.

Proton NMR spectrum (CDCl₃): δ2.7 (singlet, 6 protons), δ7.0–7.2 (multiplet, 2 protons), δ7.4–7.6 (multiplet, 2 protons), and δ9.9 (singlet, 1 proton).

Step 6 - Preparation of methyl 3-[4-(4-fluorophenyl)-2,6-dimethyl-5-pyrimidinyl]-2-propenoate 4-(4-Fluorophenyl)-2,6-dimethyl-5-pyrimidinecarboxaldehyde (31 g, 0.134 mol) and methyl(triphenylphosphoranylidene) acetate (46.6 g, 0.139 mol) in 500 mL of dichloromethane were stirred at room temperature for twenty-four hours. The solution was then concentrated and flash chromatographed on silica gel, eluting with 20% ethyl acetate/hexane, to give 36.3 g of methyl 3-[4[(4-fluorophenyl)-2,6-dimethyl-5-pyrimidinyl]-2-propenoate.

Proton NMR spectrum (CDCl₃): δ2.6 (singlet, 3 protons), δ2.7 (singlet, 3 protons), δ3.7 (singlet, 3 protons), δ5.9 (doublet, 1 proton), and δ7.0–7.7 (multiplet, 5 protons).

Step 7—Preparation of (E)-3-[4-(fluorophenyl)-2,6-dimethyl-5-pyrimidinyl]-2-propen-1-ol To a solution of 30 g( 0.104 mol) of methyl 3-[4-(4-fluorophenyl)-2,6-dimethyl-5-pyrimidinyl]-2-propenoate in 400 mL of dichloromethane at −78° C. under nitrogen was added, in a dropwise manner, 231 mL of a 1M solution of diisobutylaluminum hydride (0.231 mol). The resulting solution was stirred at −78° C. for one hour, after which the reaction was quenched by the addition of a saturated solution containing 38.0 g (0.231 mol) of sodium sulfate. The mixture was stirred vigorously, filtered through Celite®, and the filter cake washed with chloroform. The filtrate and washings were combined, dried over anhydrous magnesium sulfate, filtered, and evaporated to yield 26.6 g of (E)-3-[4-

(fluorophenyl)-2,6-dimethyl-5-pyrimidinyl]-2-propen-1-ol.

Proton NMR spectrum (CDCl$_3$): δ2.5 (singlet, 3 protons), δ2.7 (singlet, 3 protons), δ4.0 (broad multiplet, 2 protons), δ5.5–5.8 (doublet of triplets, 1 proton), δ6.2–6.5 (doublet, 1 proton), δ6.9–7.1 (multiplet, 2 protons), and δ7.4–7.6 (multiplet, 2 protons).

Step 8 - Preparation of (E)-3-[4-(4-fluorophenyl)-2,6-dimethyl-5-pyrimidinyl]-2-propenal A solution of oxalyl chloride (10.3 mL, 0.118 mol) in 40 mL of dichloromethane was cooled to -78° C. under a nitrogen atmosphere. A solution of dimethylsulfoxide (16.8 mL, 0.236 mol) in 20 mL of dichloromethane was added dropwise with stirring over a period of two minutes. Five minutes after addition was complete, a solution of 27.72 g (0.107 mol) of (E)-3-[4-(fluorophenyl)-2,6-dimethyl-5-pyrimidinyl]-2-propen-1-ol in 100 mL of dichloromethane was added dropwise. This solution was stirred at −78° C. for thirty minutes and then 75 mL (0.537 mol) of triethylamine was added and the cooling bath removed.

The mixture was allowed to warm to room temperature and the reaction was quenched by the addition of 200 mL of saturated ammonium chloride solution. The organic layer was separated and the aqueous layer was extracted with chloroform. The combined organic layers were washed with water and then brine solution, dried over anhydrous magnesium sulfate, and evaporated to yield 21.27 g of (E)-3-[4-(4-fluorophenyl)-2,6-dimethyl-5-pyrimidinyl]-2-propenal.

Proton NMR spectrum (CDCl$_3$): δ2.6 (singlet, 3 protons), δ2.7 (singlet, 3 protons), δ6.1–6.4 (multiplet, 1 proton), δ7.0–7.6 (multiplet, 5 protons), and δ9.5 (doublet, 1 proton).

Step 9—Preparation of [R*, S* (E)]-7-[4-(4-fluorophenyl)-2,6-dimethyl-5-pyrimidinyl]-5-hydroxy-3-oxo-6-heptenoic acid, ethyl ester A solution of ethyl acetoacetate (11.65 mL, 0.0914 mol) in 50 mL of anhydrous tetrahydrofuran was added dropwise with stirring to a suspension of sodium hydride (2.39 g, 0.0992 mol) in anhydrous tetrahydrofuran at 0° C. under nitrogen. The resulting mixture was stirred at 0° C. for ten minutes, after which n-butyl lithium (38.1 mL, 2.4M solution in tetrahydrofuran, 0.0914 mol) was added dropwise. The resulting orange solution was stirred for an additional ten minutes and then cooled to −78° C. A solution of (E)-3-[4-(4-fluorophenyl)-2,6-dimethyl-5-pyrimidinyl]-2-propenal (21.27 g, 0.083 mol) in 100 mL of anhydrous tetrahydrofuran was added dropwise. The resulting solution was stirred for thirty minutes, and the cooling bath was removed, after which the reaction was quenched by the addition of 12 mL of glacial acetic acid.

The pale orange solution was then stirred at room temperature for two hours after which it was partitioned between diethyl ether and water. The organic layer was separated, washed successively with saturated sodium bicarbonate solution, water, and brine solution, dried, and evaporated. This yielded 33.7 g of [R*, S* (E)]-7-[4-(4-fluorophenyl)-2,6-dimethyl-5-pyrimidinyl]-5-hydroxy-3-oxo-6-heptenoic acid, ethyl ester. Flash chromatography on silica gel, eluting with 10% methanol/chloroform yielded 27.5 g of pure material.

Proton NMR spectrum (CDCl$_3$): δ1.2 (triplet, 3 protons), δ2.4 (singlet, 3 protons), δ2.5 (doublet, 2 protons), δ2.6 (singlet, 3 protons), δ3.4 (singlet, 2 protons), δ4.1 (quartet, 2 protons), δ4.5 (multiplet, 1 proton), δ5.5 (doublet of doublets, 1 proton), δ6.5 (doublet, 1 proton), and δ6.9–7.5 (multiplet, 4 protons).

Step 9—Preparation of [R*, S* (E)]-7-[4-(4-fluorophenyl)-2,6-dimethyl-5-pyrimidinyl]-3,5-dihydroxy-6-heptenoic acid, ethyl ester To a solution of 27.5 g (0.071 mol) of [R*, S* (E)]-7-[4-(4-fluorophenyl)-2,6-dimethyl-5-pyrimidinyl]-5-hydroxy-3-oxo-6-heptenoic acid, ethyl ester and 0.73 g (0.0071 mol) of pivalic acid in 140 mL of anhydrous tetrahydrofuran under a dry air atmosphere at room temperature was added a 1M solution of triethylborane (28.4 mL, 0.0784 mol) in a dropwise manner. This solution was stirred for five minutes before 20 mL of air was bubbled through the solution. The mixture was then cooled to −78° C. and 18 mL of methanol and 2.96 g (0.0784 mol) of sodium borohydride were added. This mixture was stirred at −78° C. for six hours and then poured into 140 mL of ice cold 30% hydrogen peroxide solution at 0° C. This mixture was stirred at room temperature overnight and then diluted with water and extracted with ethyl acetate.

The organic layer was separated, washed extensively with water and brine solution, dried over anhydrous magnesium sulfate and evaporated to yield 25.7 g of [R*, S* (E)]-7-[4-(4-fluorophenyl)-2,6-dimethyl-5-pyrimidinyl]-3,5-dihydroxy-6-heptenoic acid, ethyl ester which was used in the next step without further purification.

Step 10—Preparation of [R*, S* (E)]-7-[4-(4-fluorophenyl)-2,6-dimethyl-5-pyrimidinyl]-3,5-dihydroxy-6-heptenoic acid, and the sodium salt

[R*, S* (E)]-7-[4-(4-fluorophenyl)-2,6-dimethyl-5-pyrimidinyl]-3,5-dihydroxy-6-heptenoic acid, ethyl ester (25.7 g) was dissolved in 300 mL of tetrahydrofuran and 30 mL of methanol and 66.2 mL of 1M sodium hydroxide solution (0.0662 mol) was added in one portion at room temperature. This mixture was stirred for one hour at room temperature and then concentrated under vacuum to yield crude [R*, S* (E)]-7-[4-(4-fluorophenyl)-2,6-dimethyl-5-pyrimidinyl]-3,5-dihydroxy-6-heptenoic acid, sodium salt, melting range 135°–150° C.

The salt was taken up in water, acidified with 6M hydrochloric acid, and the acidic solution extracted with ethyl acetate. The organic layer was washed successively with water and brine solution, dried over anhydrous magnesium sulfate, and evaporated to yield [R*, S* (E)]-7-[4-(4-fluorophenyl)-2,6-dimethyl-5-pyrimidinyl]-3,5-dihydroxy-6-heptenoic acid.

Step 11—Preparation of [4α, 6β(E)]-6-[2-[4-(4-fluorophenyl)-2,6-dimethyl-5-pyrimidinyl]ethenyl]tetrahydro-4-hydroxy-2H-pyran-2-one The [R*, S* (E)]-7-[4-(4-fluorophenyl)-2,6-dimethyl-5-pyrimidinyl]-3,5-dihydroxy-6-heptenoic acid from Step 10 was dissolved in a mixture of 525 mL of toluene and 175 mL of ethyl acetate and the resulting mixture was heated under reflux for five hours with the azeotropic removal of water. The reaction mixture was then cooled to room temperature, concentrated and the residue recrystallized from ethyl acetate to yield 11.14 g of

[4α, 6β(E)]-6-[2-[4-(4-fluorophenyl)-2,6-dimethyl-5-pyrimidinyl]ethenyl]tetrahydro-4-hydroxy-2H-pyran-2-one, mp 145°–147° C.

Proton NMR spectrum (CDCl₃): δ1.6–1.9 (multiplet, 2 protons), δ2.57 (singlet, 3 protons), δ2.6 (singlet, 3 protons), δ2.7 (singlet, 3 protons), δ4.3 (multiplet, 1 proton), δ5.2 (multiplet, 1 proton), δ5.6 doublet of doublets, 1 proton), δ6.6 (doublet, 1 proton), δ7.1–7.3 (multiplet, 2 protons), and δ7.5–7.6 (multiplet, 2 protons).

Infrared spectrum (KBr pellet): Principal absorption peaks at 3250, 1737, 1606, 1545, 1511, 1422, 1358, 1230, 1160, 1069, and 1037 cm$^{-1}$ $^{1}$.

EXAMPLE 2

Preparation of [4α,6β(E)]-6-[2-[4-(3,5-Dimethylphenyl)-6-methyl-2-phenyl-5-pyrimidinyl]ethenyl]-tetrahydro-4-hydroxy-2H-pyran-2-one and [R*, S*-(E)]-7-[4-(4-Fluorophenyl)-2,6-dimethyl-5-pyrimidinyl]-3,5-dihydroxy-6-heptenoic acid Employing the general method of Example 1, but employing 3,5-dimethylbenzaldehyde and benzamidine hydrochloride in Step 1, there was obtained [R*, S* (E)]-7-[4-(4-fluorophenyl)-2,6-dimethyl-5-pyrimidinyl]-3,5-dihydroxy-6-heptenoic acid, as the sodium salt, melting range 214°–220° (dec) and [4α,6β(E)]-6-[2-[4-(3,5-dimethylphenyl)-6-methyl-2-phenyl-5-pyrimidinyl-]ethenyl]tetrahydro-4-hydroxy-2H-pyran-2-one, mp 145°–147° C.

EXAMPLE 3

Preparation of [R*, S*-(E)]-7-[4-(4-Fluorophenyl)-6-methyl-2-phenyl-5-pyrimidinyl]-3,5-dihydroxy-6-heptenoic acid and [4α,6δ(E)]-6-[2-[4-(4-Fluorophenyl)-6-methyl-2-phenyl-5-pyrimidinyl]ethenyl]tetrahydro-4-hydroxy-2H-pyran-2-one Employing the general methods of Example 1, there was obtained [R*, S*-(E)]-7-[4-(4-fluorophenyl)-6-methyl-2-phenyl-5-pyrimidinyl]-3,5-dihydroxy-6-heptenoic acid as the sodium salt, melting range 110°–120° C. and [4α, 6δ(E)]-6-[2-[4-(4-fluorophenyl)-6-methyl-2-phenyl-5-pyrimidinyl]-ethenyl]tetrahydro-4-hydroxy-2H-pyran-2-one, mp 165°–167° C.

What is claimed is:

1. A compound of structural formula I

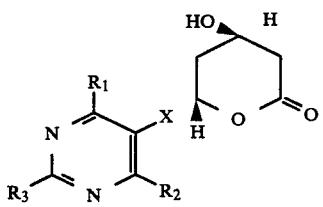

wherein X is —CH2CH2— or —CH=CH—;

R₁ and R₂ are independently selected from hydrogen; alkyl of from one to six carbons; alkoxy of from one to four carbon atoms; trifluoromethyl; cyclopropyl; cyclohexyl; cyclohexylmethyl; phenyl; phenyl substituted with fluorine, chlorine, bromine, hydroxy, trifluoromethyl, alkyl of from one to four carbon atoms, or alkoxy of from one to four carbon atoms; phenylmethyl; or phenylmethyl substituted with fluorine, chlorine, bromine, hydroxy, trifluoromethyl, alkyl of from one to four carbon atoms, or alkoxy of from one to four carbon atoms;

R₃ is hydrogen; alkyl of from one to six carbon atoms; trifluoromethyl; cyclopropyl; phenyl; or phenyl substituted with fluorine, chlorine, bromine, hydroxy, trifluoromethyl, alkyl of from one to four carbon atoms, or alkoxy of from one to four carbon atoms.

2. A compound as defined by claim 1 wherein X is —CH=CH—.

3. A compound as defined by claim 1 wherein X is —CH2CH2—.

4. A compound as defined by claim 1 having the name [4α,6δ(E)]-6-[2-[4-(4-fluorophenyl)-2,6-dimethyl-5-pyrimidinyl]ethenyl]tetrahydro-4-hydroxy-2H-pyran-2-one.

5. A compound as defined by claim 1 having the name [4α,6δ(E)]-6-[2-[4-(4-fluorophenyl)-6-methyl-2-phenyl-5-pyrimidinyl]ethenyl]tetrahydro-4-hydroxy-2H-pyran-2-one.

6. A compound as defined by claim 1 having the name [4α,6δ(E)]-6-[2-[4-(3,5-dimethylphenyl)-6-methyl-2-phenyl-5-pyrimidinyl]ethenyl]tetrahydro-4-hydroxy-2H-pyran-2-one.

7. A pharmaceutical composition for inhibiting cholesterol biosynthesis comprising an effective amount of a compound as defined by claim 1 in combination with a pharmaceutically acceptable carrier.

8. A method of inhibiting cholesterol biosynthesis in a patient in need of said treatment comprising administering a cholesterol synthesis inhibiting amount of a compound as defined by claim 1 in combination with a pharmaceutically acceptable carrier.

* * * * *

UNITED STATES PATENT AND TRADEMARK OFFICE
CERTIFICATE OF CORRECTION

PATENT NO. : 4,868,185
DATED : September 19, 1989
INVENTOR(S) : Chucholowski, et al.

It is certified that error appears in the above—identified patent and that said Letters Patent is hereby corrected as shown below:

Column 16

Claim 1, Formula I should read

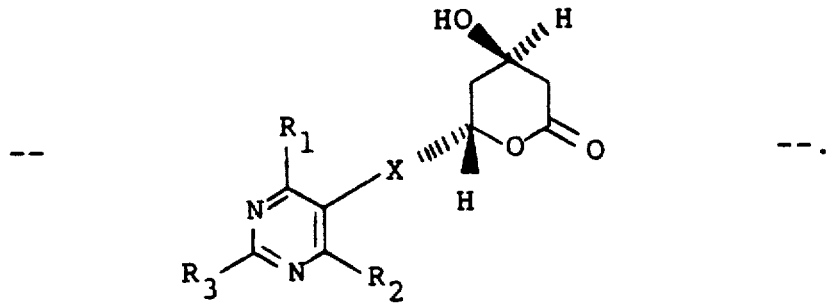

Claim 4, line 34 should read --
[4α,6β(E)]-6-[2-[4-(4-fluorophenyl)-2,6-
dimethyl-5- --.

Claim 5, line 38 should read --
[4α,6β(E)]-6-[2-[4-(4-fluorophenyl)-6-methyl-
2-phenyl- --.

UNITED STATES PATENT AND TRADEMARK OFFICE
CERTIFICATE OF CORRECTION

PATENT NO. : 4,868,185

DATED : September 19, 1989

INVENTOR(S) : Chucholowski, et al.

It is certified that error appears in the above-identified patent and that said Letters Patent is hereby corrected as shown below:

Column 16

Claim 6, line 42 should read --
[4α,6β(E)]-6-[2-[4-(3,5-dimethylphenyl)-6-methyl-2- -- .

Signed and Sealed this

Tenth Day of July, 1990

Attest:

HARRY F. MANBECK, JR.

*Attesting Officer*  *Commissioner of Patents and Trademarks*

Notice of Adverse Decision in Interference

In Interference No. 102,455, involving Patent No. 4,868,185, A. W. Chucholowski, B. D. Roth, D. R. Sliskovic, 6-(((SUBSTITUTED) PYRIMIDINYL) ETHYL)-AND ETHENYL)TETRAHYDRO-4-HYDROXYPYRAN-2-ONE INHIBITORS OF CHOLESTEROL BIOSYNTHESIS, final judgement adverse to the patentees was rendered Jan. 9, 1991, as to claims 1-8.

*(Official Gazette March 5, 1991)*